(12) United States Patent
Zhang et al.

(10) Patent No.: US 9,309,019 B2
(45) Date of Patent: Apr. 12, 2016

(54) LOW DOSE GAMMA STERILIZATION OF LIQUID ADHESIVES

(75) Inventors: Sheng Zhang, Hickory, NC (US); Rafael Ruiz, Sr., Hudson, NC (US)

(73) Assignee: Adhezion Biomedical, LLC, Wyomissing, PA (US)

(*) Notice: Subject to any disclaimer, the term of this patent is extended or adjusted under 35 U.S.C. 154(b) by 1223 days.

(21) Appl. No.: 13/112,483

(22) Filed: May 20, 2011

(65) Prior Publication Data

US 2011/0283662 A1 Nov. 24, 2011

Related U.S. Application Data

(60) Provisional application No. 61/347,213, filed on May 21, 2010.

(51) Int. Cl.
*A61L 2/08* (2006.01)
*B65B 55/16* (2006.01)
*A61L 2/00* (2006.01)

(52) U.S. Cl.
CPC ............... *B65B 55/16* (2013.01); *A61L 2/0035* (2013.01)

(58) Field of Classification Search
CPC ........................................................ A61L 2/081
USPC ............................................................ 422/22
See application file for complete search history.

(56) References Cited

U.S. PATENT DOCUMENTS

| | | | |
|---|---|---|---|
| 211,104 A | 1/1879 | Mulford |
| 334,046 A | 1/1886 | Pinkham |
| 1,221,227 A | 4/1917 | Shulz |
| 1,229,195 A | 6/1917 | Hamilton |
| 1,234,844 A | 7/1917 | Williams |
| 1,822,566 A | 9/1931 | Davies |
| 2,333,070 A | 10/1943 | Hoey et al. |
| 2,721,858 A | 10/1955 | Joyner et al. |
| 2,794,788 A | 6/1957 | Coover, Jr. et al. |
| 2,912,454 A | 11/1959 | McKeever |
| 3,152,352 A | 10/1964 | Kosik, Jr. |
| 3,254,111 A | 5/1966 | Hawkins et al. |
| 3,260,637 A | 7/1966 | von Bramer |
| 3,282,773 A | 11/1966 | Wicker, Jr. et al. |
| 3,324,855 A | 6/1967 | Heimlich |
| 3,393,962 A | 7/1968 | Andrews |
| 3,451,538 A | 6/1969 | Trementozzi |
| 3,523,628 A | 8/1970 | Colvin et al. |
| 3,524,537 A | 8/1970 | Winter |
| 3,527,224 A | 9/1970 | Rabinowitz |
| 3,527,841 A | 9/1970 | Wicker, Jr. et al. |
| 3,540,577 A | 11/1970 | Trementozzi et al. |
| 3,564,078 A | 2/1971 | Wicker, Jr. et al. |
| 3,579,628 A | 5/1971 | Gander et al. |
| 3,607,542 A | 9/1971 | Leonard et al. |
| 3,614,245 A | 10/1971 | Schwartzman |
| 3,667,472 A | 6/1972 | Halpern |
| 3,692,752 A | 9/1972 | Setsuda et al. |
| 3,742,018 A | 6/1973 | O'Sullivan |
| 3,779,706 A | 12/1973 | Nablo |
| 3,797,706 A | 3/1974 | Mule |
| 3,836,377 A | 9/1974 | Delahunty |
| 3,863,014 A | 1/1975 | Mottus |
| 3,903,055 A | 9/1975 | Buck |
| 3,924,623 A | 12/1975 | Avery |
| 3,941,488 A | 3/1976 | Maxwell |
| 3,945,383 A | 3/1976 | Bennett et al. |
| 3,975,422 A | 8/1976 | Buck |
| 3,995,641 A | 12/1976 | Kronenthal et al. |
| 4,003,942 A | 1/1977 | Buck |
| 4,012,402 A | 3/1977 | Buck |
| 4,013,703 A | 3/1977 | Buck |
| 4,038,345 A | 7/1977 | O'Sullivan et al. |
| 4,041,063 A | 8/1977 | Buck |
| 4,042,442 A | 8/1977 | Dombroski et al. |
| 4,057,535 A | 11/1977 | Lipatova et al. |
| 4,102,945 A | 7/1978 | Gleave |
| 4,105,715 A | 8/1978 | Gleave |
| 4,109,037 A | 8/1978 | Nohara |
| 4,138,040 A | 2/1979 | Stock |
| 4,142,630 A | 3/1979 | Hayes et al. |
| 4,170,585 A | 10/1979 | Motegi et al. |
| 4,171,416 A | 10/1979 | Motegi et al. |
| 4,182,823 A | 1/1980 | Schoenberg |
| 4,199,915 A | 4/1980 | Levine |
| 4,265,948 A | 5/1981 | Hayes et al. |
| 4,271,982 A | 6/1981 | Niksich et al. |
| 4,310,509 A | 1/1982 | Berglund et al. |

(Continued)

FOREIGN PATENT DOCUMENTS

DE 40 09 621 10/1991
DE 2010 3336 5/2001

(Continued)

OTHER PUBLICATIONS

"Guidance for Industry Container Closure Systems for Packaging Human Drugs and Biologics". US Department of Health and Human Services et al. May 1999.*
Cyanoacrylate MSDS. Sur-Lok Adhesives. Capture from May 13, 2008 by the Internet Archive Wayback Machine.*
"Basic Physics of Nuclear Medicine/Attenuation of Gamma-Rays". Wikibooks. previous version as appeared on Mar. 5, 2009.*
"Aclar®/Barex® Laminates: Flexible Solutions for Pharma Packaging" Drug Delivery Technology vol. 3, No. 3, May 2003, Posted on Mar. 28, 2008, http://www.drugdeliverytech.com/ME2/dirmod.asp?sid=&nm=&type=Publishing
&mod=Publications%3A%3AArticle
&mid=8F3A7027421841978F18BE895F87F791&tier=4
&id=6EC6964EB29D46D8A297E499E57A4164.

(Continued)

*Primary Examiner* — Sean E Conley
*Assistant Examiner* — Donald Spamer
(74) *Attorney, Agent, or Firm* — Stradley Ronon Stevens & Young, LLP

(57) ABSTRACT

Disclosed is a method for sterilizing adhesive 1.1-disubstituted alkylene monomer compositions, including alpha-cyanoacrylates, using low dose gamma irradiation.

17 Claims, No Drawings

(56) References Cited

U.S. PATENT DOCUMENTS

| | | |
|---|---|---|
| 4,323,557 A | 4/1982 | Rosso et al. |
| 4,328,170 A | 5/1982 | Okawara et al. |
| 4,340,043 A | 7/1982 | Seymour |
| 4,364,876 A | 12/1982 | Kimura et al. |
| 4,374,126 A | 2/1983 | Cardarelli et al. |
| 4,377,490 A | 3/1983 | Shiraishi et al. |
| 4,386,193 A | 5/1983 | Reich et al. |
| 4,408,699 A | 10/1983 | Stock |
| 4,413,753 A | 11/1983 | Stock |
| 4,439,196 A | 3/1984 | Higuchi |
| 4,444,933 A | 4/1984 | Columbus et al. |
| 4,447,224 A | 5/1984 | DeCant, Jr. et al. |
| 4,447,233 A | 5/1984 | Mayfield |
| 4,460,759 A | 7/1984 | Robins |
| 4,475,916 A | 10/1984 | Himmelstein |
| 4,480,940 A | 11/1984 | Woodruff |
| 4,486,194 A | 12/1984 | Ferrara |
| 4,487,603 A | 12/1984 | Harris |
| 4,498,609 A | 2/1985 | Stock |
| 4,507,111 A | 3/1985 | Gordon et al. |
| 4,533,422 A | 8/1985 | Litke |
| 4,542,012 A | 9/1985 | Dell |
| 4,551,366 A | 11/1985 | Maruhashi et al. |
| 4,554,686 A | 11/1985 | Baker |
| 4,643,181 A | 2/1987 | Brown |
| 4,646,765 A | 3/1987 | Cooper et al. |
| 4,649,909 A | 3/1987 | Thompson |
| 4,652,763 A | 3/1987 | Nablo |
| 4,685,591 A | 8/1987 | Schaefer et al. |
| 4,687,827 A | 8/1987 | Russo |
| 4,713,235 A | 12/1987 | Krall |
| 4,718,966 A | 1/1988 | Harris et al. |
| 4,724,177 A | 2/1988 | Russo |
| 4,772,148 A | 9/1988 | Buschemeyer |
| 4,777,085 A | 10/1988 | Murray, Jr. et al. |
| 4,784,506 A | 11/1988 | Koreska et al. |
| 4,786,534 A | 11/1988 | Aiken |
| 4,818,325 A | 4/1989 | Hiraiwa et al. |
| 4,844,250 A | 7/1989 | Holoubek et al. |
| 4,925,678 A | 5/1990 | Ranney |
| 4,959,217 A | 9/1990 | Sanders et al. |
| 4,977,892 A | 12/1990 | Ewall |
| 4,978,527 A | 12/1990 | Brink et al. |
| 4,979,638 A | 12/1990 | Bolduc |
| 4,994,542 A | 2/1991 | Matsuda et al. |
| 5,006,004 A | 4/1991 | Dirksing et al. |
| 5,009,654 A | 4/1991 | Minshall et al. |
| 5,016,784 A | 5/1991 | Batson |
| 5,018,643 A | 5/1991 | Bolduc |
| 5,031,384 A | 7/1991 | Rebeyrolle et al. |
| 5,039,753 A | 8/1991 | Woods et al. |
| 5,042,690 A | 8/1991 | O'Meara |
| 5,051,256 A | 9/1991 | Barnes |
| 5,052,585 A | 10/1991 | Bolduc |
| 5,069,907 A | 12/1991 | Mixon et al. |
| 5,083,685 A | 1/1992 | Amemiya et al. |
| 5,131,777 A | 7/1992 | Kimura et al. |
| 5,133,458 A | 7/1992 | Miller |
| 5,135,964 A | 8/1992 | Lee et al. |
| 5,154,320 A | 10/1992 | Bolduc |
| 5,167,616 A | 12/1992 | Haak et al. |
| 5,169,383 A | 12/1992 | Gyory et al. |
| 5,171,149 A | 12/1992 | Alpert |
| 5,192,536 A | 3/1993 | Huprich |
| 5,225,182 A | 7/1993 | Sharma |
| 5,226,562 A | 7/1993 | Kirk |
| 5,232,774 A | 8/1993 | Otsuka et al. |
| 5,236,703 A | 8/1993 | Usala |
| 5,240,525 A | 8/1993 | Percec et al. |
| 5,254,132 A | 10/1993 | Barley et al. |
| 5,263,615 A | 11/1993 | Anderson et al. |
| 5,283,034 A | 2/1994 | Okrongly et al. |
| 5,288,159 A | 2/1994 | Wirt |
| 5,302,629 A | 4/1994 | Berejka |
| 5,306,490 A | 4/1994 | Barley, Jr. |
| 5,312,864 A | 5/1994 | Wenz et al. |
| 5,324,131 A | 6/1994 | Gardner, III |
| 5,328,687 A | 7/1994 | Leung et al. |
| 5,344,670 A | 9/1994 | Palmer et al. |
| 5,350,798 A | 9/1994 | Linden et al. |
| 5,358,349 A | 10/1994 | Burroughs et al. |
| 5,370,221 A | 12/1994 | Magnusson et al. |
| 5,379,927 A | 1/1995 | Montenieri et al. |
| 5,403,591 A | 4/1995 | Tighe et al. |
| 5,411,345 A | 5/1995 | Ueji et al. |
| 5,453,457 A | 9/1995 | Meltzer et al. |
| 5,457,141 A | 10/1995 | Matsuda et al. |
| 5,470,597 A | 11/1995 | Mendenhall |
| 5,475,110 A | 12/1995 | Hudkins et al. |
| 5,480,935 A | 1/1996 | Greff et al. |
| 5,530,037 A | 6/1996 | McDonnell et al. |
| 5,547,662 A | 8/1996 | Khan et al. |
| 5,561,198 A | 10/1996 | Huver et al. |
| 5,649,648 A | 7/1997 | Lier et al. |
| 5,658,384 A | 8/1997 | Imlay, Jr. |
| 5,665,106 A | 9/1997 | Hammerslag |
| 5,665,107 A | 9/1997 | Hammerslag |
| 5,665,817 A | 9/1997 | Greff et al. |
| 5,684,042 A | 11/1997 | Greff et al. |
| 5,730,994 A | 3/1998 | Askill et al. |
| 5,749,665 A | 5/1998 | Kato et al. |
| 5,749,956 A | 5/1998 | Fisher et al. |
| 5,759,194 A | 6/1998 | Hammerslag |
| 5,769,552 A | 6/1998 | Kelley et al. |
| 5,803,086 A | 9/1998 | Scholz et al. |
| 5,807,563 A | 9/1998 | Askill et al. |
| 5,810,495 A | 9/1998 | McAuley |
| D402,199 S | 12/1998 | Saunders |
| 5,874,044 A | 2/1999 | Kotzev |
| 5,888,007 A | 3/1999 | Nicoll et al. |
| 5,902,594 A | 5/1999 | Greff et al. |
| 5,906,300 A | 5/1999 | Horie |
| 5,909,976 A | 6/1999 | Maeda |
| 5,916,882 A | 6/1999 | Jeng |
| 5,928,611 A | 7/1999 | Leung |
| 5,944,754 A | 8/1999 | Vacanti |
| 5,957,877 A | 9/1999 | Askill et al. |
| 5,971,225 A | 10/1999 | Kapsa |
| 5,979,450 A | 11/1999 | Baker et al. |
| 5,981,621 A | 11/1999 | Clark et al. |
| 5,985,395 A | 11/1999 | Comstock et al. |
| 5,996,796 A | 12/1999 | Kvitrud et al. |
| 5,998,472 A | 12/1999 | Berger et al. |
| 6,086,906 A | 7/2000 | Greff et al. |
| 6,090,397 A | 7/2000 | Lee et al. |
| 6,099,807 A | 8/2000 | Leung |
| 6,136,326 A | 10/2000 | Kotzev |
| 6,143,352 A | 11/2000 | Clark et al. |
| 6,143,805 A | 11/2000 | Hickey et al. |
| 6,155,265 A | 12/2000 | Hammerslag |
| 6,217,603 B1 | 4/2001 | Clark et al. |
| 6,228,354 B1 | 5/2001 | Jeng |
| 6,245,933 B1 | 6/2001 | Malofsky et al. |
| 6,248,800 B1 | 6/2001 | Greff et al. |
| 6,283,933 B1 | 9/2001 | D'Alessio et al. |
| 6,294,629 B1 | 9/2001 | O'Dwyer et al. |
| 6,299,631 B1 | 10/2001 | Shalaby |
| 6,310,166 B1 | 10/2001 | Hickey et al. |
| 6,322,852 B1 | 11/2001 | Leung |
| 6,323,275 B2 | 11/2001 | Takahashi et al. |
| 6,331,172 B1 | 12/2001 | Epstein et al. |
| 6,340,097 B1 | 1/2002 | D'Alessio et al. |
| 6,352,704 B1 | 3/2002 | Nicholson et al. |
| 6,372,313 B1 | 4/2002 | D'Alessio et al. |
| 6,376,019 B1 | 4/2002 | Leung |
| 6,425,704 B2 | 7/2002 | Voiers et al. |
| 6,428,233 B1 | 8/2002 | Clark et al. |
| 6,428,234 B1 | 8/2002 | Bobo et al. |
| 6,439,789 B1 | 8/2002 | Ballance et al. |
| 6,475,502 B1 | 11/2002 | Lee et al. |
| 6,478,191 B1 | 11/2002 | D'Alessio et al. |
| 6,488,665 B1 | 12/2002 | Severin et al. |
| 6,492,434 B1 | 12/2002 | Barley, Jr. et al. |
| 6,494,896 B1 | 12/2002 | D'Alessio et al. |

(56) References Cited

U.S. PATENT DOCUMENTS

| | | |
|---|---|---|
| 6,495,229 B1 | 12/2002 | Carte et al. |
| 6,505,985 B1 | 1/2003 | Hidle et al. |
| 6,506,464 B1 | 1/2003 | Montenieri et al. |
| 6,541,304 B1 | 4/2003 | Bouras et al. |
| 6,547,467 B2 | 4/2003 | Quintero |
| 6,547,917 B1 | 4/2003 | Misiak et al. |
| 6,550,644 B2 | 4/2003 | Cruddas |
| 6,557,731 B1 | 5/2003 | Lyon et al. |
| 6,579,469 B1 | 6/2003 | Nicholson et al. |
| 6,592,281 B2 | 7/2003 | Clark et al. |
| 6,595,940 B1 | 7/2003 | D'Alessio et al. |
| 6,616,019 B2 | 9/2003 | D'Alessio et al. |
| 6,620,846 B1 | 9/2003 | Jonn et al. |
| 6,626,296 B1 | 9/2003 | Jimu et al. |
| 6,637,967 B2 | 10/2003 | Bobo et al. |
| 6,667,031 B2 | 12/2003 | Azevedo |
| 6,672,456 B2 | 1/2004 | Russell |
| 6,676,322 B1 | 1/2004 | Leung |
| 6,676,332 B1 | 1/2004 | Hauer et al. |
| 6,699,940 B2 | 3/2004 | Shalaby |
| 6,705,467 B1 | 3/2004 | Kancsar et al. |
| 6,705,790 B2 | 3/2004 | Quintero et al. |
| 6,742,522 B1 | 6/2004 | Baker et al. |
| 6,743,858 B2 | 6/2004 | Hickey et al. |
| 6,746,667 B2 | 6/2004 | Badejo et al. |
| 6,767,552 B2 | 7/2004 | Narang |
| 6,779,657 B2 | 8/2004 | Mainwaring et al. |
| 6,797,107 B1 | 9/2004 | Kotzey |
| 6,802,416 B1 | 10/2004 | D'Alessio et al. |
| 6,811,341 B2 | 11/2004 | Crane |
| 6,817,802 B2 | 11/2004 | Nishitani et al. |
| 6,849,082 B2 | 2/2005 | Azevedo |
| 6,863,460 B2 | 3/2005 | Nicoll et al. |
| 6,881,421 B1 | 4/2005 | daSilveira et al. |
| 6,896,838 B2 | 5/2005 | D'Alessio |
| 6,942,875 B2 | 9/2005 | Hedgpeth |
| 6,960,040 B2 | 11/2005 | D'Alessio et al. |
| 6,974,585 B2 | 12/2005 | Askill |
| 6,977,278 B1 | 12/2005 | Misiak |
| 6,981,664 B1 | 1/2006 | Fugere |
| 6,995,227 B2 | 2/2006 | Ryan et al. |
| 7,040,827 B2 | 5/2006 | Gueret |
| 7,094,250 B2 | 8/2006 | Stenton |
| 7,128,241 B2 | 10/2006 | Leung |
| 7,179,008 B2 | 2/2007 | Holcomb |
| 7,255,874 B1 | 8/2007 | Bobo et al. |
| 7,297,217 B2 | 11/2007 | Dewitt |
| 7,306,390 B2 | 12/2007 | Qunitero et al. |
| RE40,003 E | 1/2008 | Bennett et al. |
| 7,316,833 B1 | 1/2008 | Galloway et al. |
| 7,371,345 B2 | 5/2008 | Stewart et al. |
| 7,441,973 B2 | 10/2008 | Voegele et al. |
| 7,516,872 B2 | 4/2009 | Boone et al. |
| 7,621,411 B2 | 11/2009 | Doherty et al. |
| 7,648,296 B2 | 1/2010 | Wong |
| 7,696,399 B2 | 4/2010 | Rogers |
| 7,704,003 B2 | 4/2010 | Ziniti et al. |
| 7,708,180 B2 | 5/2010 | Murray et al. |
| 7,744,624 B2 | 6/2010 | Bettuchi |
| 7,785,026 B2 | 8/2010 | Eng et al. |
| 8,118,508 B2 | 2/2012 | Goodman et al. |
| 8,550,737 B2 | 10/2013 | Ruiz, Sr. et al. |
| 2002/0002223 A1 | 1/2002 | Cox et al. |
| 2002/0037272 A1 | 3/2002 | Askill et al. |
| 2002/0151873 A1 | 10/2002 | Moore |
| 2003/0044380 A1 | 3/2003 | Zhu et al. |
| 2003/0077386 A1 | 4/2003 | Azevedo |
| 2003/0135016 A1 | 7/2003 | Tajima et al. |
| 2003/0149128 A1 | 8/2003 | Malofsky et al. |
| 2003/0158579 A1 | 8/2003 | Azevedo |
| 2003/0158580 A1 | 8/2003 | Azevedo |
| 2004/0115274 A1 | 6/2004 | Cox et al. |
| 2004/0120849 A1 | 6/2004 | Stewart et al. |
| 2004/0126355 A1 | 7/2004 | Childers |
| 2004/0127738 A1 | 7/2004 | Azevedo |
| 2004/0253039 A1 | 12/2004 | Stenton |
| 2005/0025559 A1 | 2/2005 | Stenton |
| 2005/0047845 A1 | 3/2005 | White et al. |
| 2005/0047846 A1 | 3/2005 | Narang et al. |
| 2005/0053578 A1* | 3/2005 | Bordoloi et al. ............ 424/78.27 |
| 2005/0054967 A1 | 3/2005 | Ashe et al. |
| 2005/0067312 A1 | 3/2005 | Gupta et al. |
| 2005/0142163 A1 | 6/2005 | Hunter et al. |
| 2005/0147457 A1 | 7/2005 | Badejo et al. |
| 2005/0147582 A1 | 7/2005 | Zimmerman et al. |
| 2005/0148998 A1 | 7/2005 | Haley |
| 2005/0175395 A1 | 8/2005 | Quintero et al. |
| 2005/0182347 A1 | 8/2005 | Bishop et al. |
| 2005/0196431 A1 | 9/2005 | Narang et al. |
| 2005/0197421 A1 | 9/2005 | Loomis |
| 2005/0256446 A1 | 11/2005 | Criscuolo et al. |
| 2005/0281866 A1 | 12/2005 | Jarrett et al. |
| 2005/0284487 A1 | 12/2005 | Gellerstedt et al. |
| 2006/0049203 A1 | 3/2006 | Boone et al. |
| 2006/0062687 A1 | 3/2006 | Morales |
| 2006/0247568 A1 | 11/2006 | Stenton |
| 2006/0282035 A1 | 12/2006 | Battisti et al. |
| 2007/0041935 A1 | 2/2007 | Salamone et al. |
| 2007/0048356 A1 | 3/2007 | Schorr et al. |
| 2007/0065334 A1 | 3/2007 | Shalaby |
| 2007/0078207 A1 | 4/2007 | Jonn et al. |
| 2007/0084144 A1 | 4/2007 | Labrecque et al. |
| 2007/0092481 A1 | 4/2007 | Misiak et al. |
| 2007/0092483 A1 | 4/2007 | Pollock |
| 2007/0131356 A1 | 6/2007 | Battisti |
| 2007/0147947 A1 | 6/2007 | Stenton et al. |
| 2007/0248486 A1 | 10/2007 | Morales |
| 2008/0021139 A1 | 1/2008 | Blacklock et al. |
| 2008/0033280 A1 | 2/2008 | Lubock et al. |
| 2008/0058863 A1 | 3/2008 | Quintero et al. |
| 2008/0069801 A1 | 3/2008 | Lee et al. |
| 2008/0078413 A1 | 4/2008 | Padget et al. |
| 2008/0095569 A1 | 4/2008 | Voegele et al. |
| 2008/0102053 A1 | 5/2008 | Childers |
| 2008/0105580 A1 | 5/2008 | Nentwick et al. |
| 2008/0121657 A1 | 5/2008 | Voegele et al. |
| 2008/0125811 A1 | 5/2008 | Bettuchi |
| 2008/0131190 A1 | 6/2008 | Goodman et al. |
| 2008/0167681 A1 | 7/2008 | Stenton |
| 2008/0195040 A1 | 8/2008 | Clark et al. |
| 2008/0241249 A1 | 10/2008 | Quintero et al. |
| 2008/0287987 A1 | 11/2008 | Boyden et al. |
| 2008/0319063 A1 | 12/2008 | Zhang |
| 2009/0257976 A1 | 10/2009 | Kerber et al. |
| 2009/0311030 A1 | 12/2009 | Stenton |
| 2009/0317353 A1 | 12/2009 | Zhang et al. |
| 2009/0318583 A1 | 12/2009 | Zhang et al. |
| 2009/0324319 A1 | 12/2009 | Houde et al. |
| 2009/0324320 A1 | 12/2009 | Houde et al. |
| 2010/0035997 A1 | 2/2010 | Broadley et al. |
| 2010/0168637 A1 | 7/2010 | Casey et al. |
| 2010/0168638 A1 | 7/2010 | Korogi et al. |
| 2010/0269749 A1 | 10/2010 | Badejo et al. |
| 2010/0274258 A1 | 10/2010 | Silvestrini et al. |
| 2011/0028883 A1 | 2/2011 | Juan, Jr. et al. |

FOREIGN PATENT DOCUMENTS

| | | | |
|---|---|---|---|
| DE | 20314688 | 11/2003 | |
| EP | 0127466 | 12/1984 | |
| EP | 0271675 | 6/1988 | |
| EP | 0364173 | * 4/1990 | ............ B01D 29/01 |
| EP | 1445032 | 8/2004 | |
| FR | 1130737 | 10/1956 | |
| FR | 2700698 | 7/1994 | |
| GB | 1016053 | 1/1966 | |
| GB | 1230560 | 5/1971 | |
| GB | 2200124 | 7/1988 | |
| JP | 5841068 | 3/1983 | |
| JP | 59-066471 | 4/1984 | |
| JP | 62-022877 | 1/1987 | |
| JP | 03-207778 | 9/1991 | |
| JP | 10-140091 | 5/1998 | |
| WO | WO96/14292 | 5/1996 | |

(56) References Cited

FOREIGN PATENT DOCUMENTS

| WO | WO96/23532 | 8/1996 |
|---|---|---|
| WO | WO99/10020 | 3/1999 |
| WO | WO03/070257 | 8/2003 |
| WO | WO2004/045498 | 6/2004 |
| WO | WO2006/073922 | 7/2006 |
| WO | WO2009/003017 | 12/2008 |
| WO | WO2009/064291 | 5/2009 |

OTHER PUBLICATIONS

Borrel et al. "The Effect of Crown Ethers, Tetraalkylammonioum Salts, and Polyoxyethylene Amphiphiles on Pirarubicin Incorporation in K562 Resistant Cells" Biochemical Pharmacology, vol. 50, No. 12., pp. 2069-2076, 1995.

Cameron, J.L. et al., "The Degradation of Cyanoacrylate Tissue Adhesive, pt. 1", Surgery, vol. 58, Iss. 2, Aug. 1965, pp. 424-430.

Canale, A.J., et al., "Methyl a-cyanoacrylate. I. Free-radical homopolymerization", Journal of Applied Polymer Science, vol. 4, No. 11, Sep./Oct. 1960, pp. 231-236 [Abstract Only].

Collins et al., "Biological Substrates and Cure Rates of Cyanoacrylate Tissue Adhesives" Archives of Surgery vol. 93, Sep. 1966, 428-432.

Darwish et al., "The evaluation of crown ether based niosomes as cation containing and cation sensitive drug delivery systems" International Journal of Pharmaceutics 159 (1997) 207-213.

Dumont et al., "New Oligosaccharidic Crown Ethers as Potential Drug-Targetting Vectors: Synthesis & Biological Evaluation" Bioorganic & Medicinal Chemistry Letters, vol. 4, No. 9, pp. 1123-1126, 1994.

Fussnegger, B. "Poloxamers (1) Lutrol® F 68 (Poloxamer 188)." BASF ExAct, Nov. 1999, 5-6.

Garnier-Suillerot et al., "Analysis of Drug Transport Kinetics in Multidrug-resistant Cells: Implications for Drug Action" Current Medicinal Chemistry, 2001, 8, 51-64.

Hansen, "Fast Cure—High moisture vapor transmission rate adhesives improve wound care." Adhesives Age Mar. 2003, 22, 24-25.

International Search Report and Written Opinion dated Dec. 8, 2010 for international application No. PCT/US2009/062761.

Lehman et al., "Toxicity of Alkyl 2-Cyanoacrylates", Archives of Surgery, vol. 93, Issue 3, Sep. 1966, pp. 441-446.

Leonard, F, "Hemostatic Applications of Alpha Cyanoacrylates: Bonding Mechanism and Physiological Degradation of Bonds", Adhesion in Biological Systems, ed. R.S. Manly, 1970, pp. 185-199.

Leonard, F. et al., "Interfacial Polymerization of n-Alkyl a-Cyanoacrylate Homologs", Journal of Applied Polymer Science, vol. 10 1966, pp. 1617-1623.

Leonard, F. et al., "Synthesis and Degradation of Poly (alkyl a-Cyanoacrylates)", Journal of Applied Polymer Science, vol. 10, Iss 8, Aug. 1966, p. 1214.

Leonard, F. et al., "Synthesis and Degradation of Poly(alkyl a-Cyanoacrylates)", Journal of Applied Polymer Science, vol. 10, Iss. 2, Feb. 1966, pp. 259-272.

Material Safety Data Sheet (MSDS) of 2-octyl cyanoacrylate; Jun. 2, 2004.

Material Safety Data Sheet (MSDS) of isobuthyl-2-cyanoacrylate; Sep. 25, 1998.

Material Safety Data Sheet (MSDS) of n-butyl cyanoacrylate; Oct. 19, 2009 and Jun. 2, 2004.

Quinn, J.V., "Clinical Approaches to the Use of Cyanoacrylate Tissue Adhesives", Tissue Adhesives in Clinical Medicine, Second Edition, 2005, BC Decker, Inc., pp. 27-76.

Tseng, Y.C. et al., "Modification of synthesis and investigation of properties for 2-cyanoacrylates", Biomaterials, vol. 11, Jan. 1990, pp. 73-79.

Uchegbu et al., "Non-ionic surfactant based vesicles (niosomes) in drug delivery" International Journal of Pharmaceutics 172 (1998) 33-70.

Vezin, W.R. et al., "Diffusion of Small Molecules in Poly-n-Alkyl Cyanoacrylates", British Pharmaceutical Conference 1978—Communications presented at the 115th meeting, Coventry, Sep. 11-15, 1978, Journal of Pharmacy and Pharmacology, vol. 30, Issue: Suppl, Dec. 1978, p. 2P.

Vezin, W.R. et al., "In vitro heterogeneous degradation of poly(n-alkyl a-cyanoacrylates)", Journal of Biomedical Materials Research, vol. 14, 1980, pp. 93-106.

Woodward, S.C. et al., "Histotoxicity of Cyanoacrylate Tissue Adhesives in the Rat", Annals of Surgery, vol. 162, No. 1, Jul. 1965, pp. 113-122.

Yonezawa, M. et al., "Studies on a-Cyanoacrylate, VI: Reaction of Cyanoacetate with Formaldehyde" Yuki Gosei Kagaku Kyokaishi, vol. 25, Iss 4, Apr. 1967, pp. 311-316.

* cited by examiner

LOW DOSE GAMMA STERILIZATION OF LIQUID ADHESIVES

CROSS-REFERENCE TO RELATED APPLICATIONS

This application claims the benefit of priority under 35 U.S.C. §119(e) to earlier filed U.S. provisional patent application Ser. No. 61/347,213, filed on May 21, 2010, the disclosure of which is incorporated herein by reference in its entirety.

FIELD OF THE INVENTION

The present invention is directed to a method of sterilizing cyanoacrylate adhesive compositions using lower dose gamma irradiation. The compositions are suitable for bonding a wide range of substrates but are especially intended for medical and/or veterinary uses such as wound closure and surgical applications.

BACKGROUND OF THE INVENTION

Monomer and polymer adhesives have found wide use in many applications, including industrial, consumer household, as well as medical applications. Included among these adhesives are the 1,1-disubstituted ethylene monomers and polymers, such as the alpha-cyanoacrylates. Since the discovery of the adhesive properties of such monomers and polymers, they have found wide use due to the speed with which they cure, the strength of the resulting bond formed, and their relative ease of use. These characteristics have made the alpha-cyanoacrylate adhesives the primary choice for numerous applications such as bonding plastics, rubbers, glass, metals, wood and, more recently, biological tissues.

It is known that monomeric forms of alpha-cyanoacrylates are extremely reactive, polymerizing rapidly in the presence of even minute amounts of an initiator, including moisture present in the air or on moist surfaces such as animal, including human, tissue. Once polymerization has been initiated, the cure can be very rapid. In general, these cyanoacrylates can be extremely sensitive making them challenging to work with and to store.

Medical applications of 1,1-disubstituted ethylene adhesive compositions include use as an alternative or an adjunct to surgical sutures and/or staples in wound closure, as well as for covering and protecting surface wounds such as lacerations, abrasions, burns, minor cuts or other wounds. When an adhesive is applied to surfaces to be joined, it is usually applied in its monomeric form, and the resultant polymerization gives rise to the desired adhesive bond. Additionally, these adhesives have found use as sealants, and protective coverings to immobilize microbes prior to surgery as a surgical drape, to prevent blister formation, or undesirable effects from radiation.

When such adhesive compositions, and the applicators used to apply the adhesive, are desired to be used in the medical arts, it is often required, or at least preferred, that they be sterile. It is also desirable that the composition retain a shelf life of one to two years and that the container or applicator in which it is stored does not react with or adversely affect the composition and its performance, particularly after sterilization.

A variety of sterilization methods are generally used to sterilize monomeric and polymeric compositions as well as their containers or applicators. These methods include chemical, physical, and irradiation techniques. Examples of chemical methods include exposure to ethylene oxide or hydrogen peroxide vapor. Physical methods of sterilization may include, for example, sterilization by dry or moist heat. Gamma irradiation, electron beam (e-beam) irradiation, and microwave irradiation are some common examples of irradiation methods. Aseptic filling may also be used to provide sterile compositions.

The process of gamma sterilization is extremely thorough and can be used on sealed packages, a package's contents and outer wrap all of which can be fully sterilized after assembling, requiring no post-processing cooling. Gamma sterilization's downside is that it can alter the physical properties of the component package materials and alter the adhesive contained inside. Gamma sterilization is a robust process, especially at the prescribed doses of a minimum of 25 kGy, as taught in U.S. Pat. No. 5,530,037 to McDonnell et al., and can cause premature polymerization of the monomers. In addition, many additive substances, for example polymers used as thickeners, undergo degradation resulting in unwanted contaminants or properties of the resulting substance. This significantly limits the formulator's ability to formulate adhesive compositions which have the desirable stability and flow characteristics, and which can be sterilized.

Lower dose irradiation (gamma or electron beam irradiation less than 10 kGy) is taught in U.S. Patent Application Publication No. 2007/0065334 to Shalaby. However it is used to generate gaseous formaldehyde which in turn sterilizes cyanoacrylate adhesives. The radiochemical sterilization utilized is a costly, complicated hybrid sterilization process encompassing chemical and radiation sterilization using a precisely radiolytically generated gaseous formaldehyde, in combination with a complex packaging system with specialized holders for the adhesive packages.

Other references teach using lower dose irradiation to sterilize 2-cyanoacrylate ester adhesive compositions utilizing electron beam irradiation. U.S. Patent Application Publication No. 2007/0248486 to Morales discloses sterilizing 2-cyanoacrylate ester adhesive compositions using a dose of 1 to 15 kGy and specifically state that the combination of the monomeric 2-cyanoacrylate and electron beam irradiation together have a lethal effect on microbials. And, U.S. Pat. No. 6,143,805 to Hickey et al. teaches an e-beam dosage as 5-100 kGy, preferably about 10-50 kGy, and more preferably 20-30 kGy to sterilize cyanoacrylates, with an optional post gamma irradiation step at an undisclosed dose.

U.S. Pat. No. 6,248,800 to Greff et al. discloses a method for sterilizing cyanoacrylate ester compositions at room temperature using lower irradiation doses of electron beam irradiation of preferably 15 to 20 kGy, but also includes the limitation that the average bulk density of the materials comprising the packaging elements can be no more than about 0.2 $g/cm^3$.

U.S. Pat. No. 7,371,345 to Stewart et al. utilizes dry heat and low dose e-beam and gamma irradiation to sterilize cyanoacrylate adhesive compositions and kits but in multiple packages and steps. The components of an adhesive composition are packaged and separated from each other, or a composition is separated from other kit components, and each are individually sterilized in series and/or in parallel using any sterilization method, including e-beam and gamma, at doses (same or different) such that the cumulative dose of any component is not excessive so as to alter the components' properties. Such a method avoids the problem of some adhesive compositions not being able to be fully sterilized as a single composition, because certain of the component materials react adversely to the sterilization process.

As the use of cyanoacrylate adhesives in the medical field continues to grow, the need exists for new and improved ways to utilize readily available gamma sterilization technology to sterilize cyanoacrylate adhesives without encountering disadvantageous complicated packaging systems, expensive components or complex methods.

SUMMARY OF THE INVENTION

The present invention is directed to a new and unexpected discovery that curable alpha-cyanoacrylate adhesive monomers which have been purified using a particulate material, can be effectively sterilized at relatively low doses of gamma irradiation in practical sealed containers having a nitrile polymer lining, to produce an adhesive composition with an extended shelf life making them particularly suitable for medical applications.

In one aspect, the present invention provides a method for preparing a polymerizable, sterile, cyanoacrylate adhesive composition, the method comprising the steps of: (a) filtering a cyanoacrylate adhesive composition through a filter having a pore size of from about 1 to about 200 μm under an inert and moisture-free atmosphere; (b) adding the cyanoacrylate adhesive composition from (a) to individual packaging elements, each individual packaging element having a density and comprising multiple layers; (c) packaging the individual packaging elements into at least one outer package having a density; and (d) sterilizing the cyanoacrylate adhesive composition and the individual packaging elements by exposing the individual packaging elements to gamma radiation at a dose of from about 5 to about 20 kGy, wherein the total density of the individual packaging elements and the at least one outer package is from about 0.05 to about 0.6 gm/cm³.

In another aspect, the present invention provides a method for preparing a sterile, cyanoacrylate monomer composition in a sealed container using low dose gamma irradiation, wherein the method comprises: treating said cyanoacrylate monomer composition with a particulate pyrrolidone polymer to obtain a purified cyanoacrylate monomer composition; isolating the purified cyanoacrylate monomer composition from the particulate pyrrolidone polymer; stabilizing the isolated monomer composition with at least one anionic stabilizer and at least one free radical stabilizer to obtain a stabilized monomer composition; adding the stabilized cyanoacrylate monomer composition to a package comprising multiple layers with the inner layer comprising a nitrile polymer; sealing said package containing the cyanoacrylate monomer composition; irradiating said package and said cyanoacrylate monomer composition with gamma irradiation at a dose of from about 5 to about 20 kGy.

DETAILED DESCRIPTION OF PREFERRED EMBODIMENTS

The present invention provides a method for preparing a polymerizable, sterile, cyanoacrylate adhesive composition, the method comprising the steps of: (a) filtering a cyanoacrylate adhesive composition through a filter having a pore size of from about 1 to about 200 μm under an inert and moisture-free atmosphere; (b) adding the cyanoacrylate adhesive composition from (a) to individual packaging elements, each individual packaging element having a density and comprising multiple layers; (c) packaging the individual packaging elements into at least one outer package having a density; and (d) sterilizing the cyanoacrylate adhesive composition and the individual packaging elements by exposing the individual packaging elements to gamma radiation at a dose of from about 5 to about 20 kGy, wherein the total density of the individual packaging elements and the at least one outer package is from about 0.05 to about 0.6 gm/cm³.

As used herein, the term "cyanoacrylate adhesive composition" or "cyanoacrylate adhesive compositions" refers to polymerizable formulations comprising polymerizable cyanoacrylate ester monomers for use as medical adhesives and sealants.

The adhesive compositions of the present invention are based upon one or more polymerizable cyanoacrylate monomers and/or reactive oligomers. These monomers are readily anionically polymerizable, or free radical polymerizable, to form polymers. Cyanoacrylate monomers suitable for use in accordance with the present invention include, but are not limited to, 1,1-disubstituted ethylene monomers of the formula:

wherein X and Y are each strong electron withdrawing groups, and R is H, —CH=CH₂ or, provided that X and Y are both cyano groups, or a $C_1$-$C_4$ alkyl group.

Examples of monomers within the scope of formula (I) include alpha-cyanoacrylate's, vinylidene cyanides, $C_1$-$C_4$ alkyl homologues of vinylidene cyanides, dialkyl methylene malonates, acylacrylonitriles, vinyl sulfinates and vinyl sulfonates of the formula CH2=CX'Y wherein X' is —SO₂R' or —SO₃R' and Y' is —CN, —COOR', —COCH₃, —SO₂R' or —SO₃R', and R' is H or hydrocarbyl.

Preferred monomers of formula (I) for use in this invention are alpha-cyanoacrylates. These monomers are known in the art and have the formula

wherein $R^2$ is hydrogen and $R^3$ is a hydrocarbyl or substituted hydrocarbyl group; a group having the formula —$R^4$—O—$R^5$—O—$R^6$, wherein $R^4$ is a 1,2-alkylene group having 2-4 carbon atoms, $R^5$ is an alkylene group having 2-12 carbon atoms, and $R^6$ is an alkyl group having 1-6 carbon atoms; or a group having the formula

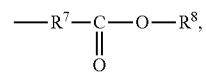

wherein $R^7$ is

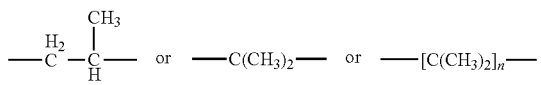

wherein n is 1-10, preferably 1-8 carbon atoms and $R^8$ is an organic moiety. Preferred alpha-cyanoacrylates are ones having an alkyl chain length of from about 1 to about 20 carbon atoms or more preferably from about 3 to about 8 carbon atoms. The preferred cyanoacrylates are n-butyl and 2-octyl cyanoacrylate, or mixtures thereof.

Examples of suitable hydrocarbyl and substituted hydrocarbyl groups include straight chain or branched chain alkyl groups having 1-16 carbon atoms; straight chain or branched chain $C_1$-$C_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

The organic moiety $R^8$ may be substituted or unsubstituted and may be straight chain, branched or cyclic, saturated, unsaturated or aromatic. Examples of such organic moieties include $C_1$-$C_8$ alkyl moieties, $C_2$-$C_8$ alkenyl moieties, $C_2$-$C_8$ alkynyl moieties, C3-C12 cycloaliphatic moieties, aryl moieties such as phenyl and substituted phenyl and aralkyl moieties such as benzyl, methylbenzyl and phenylethyl. Other organic moieties include substituted hydrocarbon moieties, such as halo (e.g., chloro-, fluoro-, and bromo-substituted hydrocarbons) and oxy- (e.g., alkoxy substituted hydrocarbons) substituted hydrocarbon moieties. Preferred organic radicals are alkyl, alkenyl and alkynyl moieties having from 1 to about 8 carbon atoms, and halo-substituted derivatives thereof. Particularly preferred are alkyl moieties of 4 to 6 carbon atoms.

In the cyanoacrylate monomer of the formula (II), $R^3$ is preferably an alkyl group having 1-10 carbon atoms or a group having the formula -$AOR^9$, wherein A is a divalent straight or branched chain alkylene or oxyalkylene moiety having 2-8 carbon atoms, and $R^9$ is a straight or branched alkyl moiety having 1-8 carbon atoms.

Examples of groups represented by the formula -$AOR^9$ include 1-methoxy-2-propyl, 2-butoxy ethyl, isopropoxy ethyl, 2-methoxy ethyl, and 2-ethoxy ethyl.

The preferred alpha-cyanoacrylate monomers used in this invention are 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate, or a combination thereof.

The alpha-cyanoacrylate monomer of formula (II) of the present invention can be prepared according to methods known in the art. U.S. Pat. Nos. 2,721,858, 3,254,111, and 4,364,876, each of which is hereby incorporated in its entirety by reference herein, disclose methods for preparing alpha-cyanoacrylates. One such process includes, for example, reacting a cyanoacetate with formaldehyde in the presence of a basic condensation catalyst at an elevated temperature to produce a low molecular weight polymer. A de-polymerization (or cracking) step is followed under high temperature and high vacuum in the presence of acidic and anionic inhibitors, yielding a crude monomer that can be distilled under high temperature and high vacuum in the presence of radical and acidic inhibitors.

In preferred embodiments of the present invention, after synthesis of the monomer and prior to formulating the final composition the amount of contaminants and extraneous additives are reduced and/or removed. This renders the resultant compositions highly susceptible to polymerization when applied to a substrate and also substantially eliminates the potential for toxic by-products to form from otherwise high levels of stabilizers or other contaminants upon gamma irradiation. Without being bound to any single specific mechanism, this process relies on a combination of physical adsorption/absorption, chemical reaction, and hydrogen bonding of the acid group(s) onto particulate surfaces. The process requires acid removing particulate substances be in fluid contact with the excessively stabilized monomer(s) and be insoluble or otherwise isolatable from the monomers, such as by filtration, centrifugation, phasing out, membrane separation, or other appropriate isolating mechanism. The particulate substance can be any pyrrolidone polymer. The preferred particulate substance is one comprising vinyl pyrrolidone copolymer. Thus, acids or other stabilizers and contaminants are isolated or removed from the monomers. This process is described in detail in U.S. Pat. Nos. 6,667,031 and 6,849,082 which are incorporated herein by reference. The resulting purified monomers are then stabilized to the desired level.

In a preferred embodiment of the invention, particulate vinyl pyrrolidone polymers and copolymers are applied to the monomer to reduce the amount of contaminants and extraneous additives. These particulates are combined with the monomer adhesive in mutual contact until the adhesive is destabilized. In order to achieve the mutual contact, vinyl pyrrolidone polymer is mixed with the cyanoacrylate monomer under vacuum for a minimum of three (3) hours to destabilize the adhesive. The solid powder of vinyl pyrrolidone polymer and undesirable contaminants are then removed from the cyanoacrylate adhesive by filtering through a filter. The particulate agent and undesirable contaminants are then separated from the cyanoacrylate monomers by an isolation process of filtration. Once isolated, the cyanoacrylate monomers are re-stabilized with the desirable stabilizers at desirable levels, usually lower than prior to the treatment, to provide the final stable adhesive or sealant compositions, which will have desirable cure rates in the five (5) seconds to approximately one minute range. These cure rates are particularly suitable for medical applications of the adhesive compositions.

In preferred embodiments of the present invention, the cyanoacrylate adhesive compositions comprise at least one anionic stabilizer and at least one free radical stabilizer. Preferably, the amount of anionic stabilizer employed is in the range of from about 2 to about 50 ppm.

The preferred anionic stabilizer is sulfur dioxide ($SO_2$) in an amount of about 2 to about 50 ppm, preferably about 5 to about 50 ppm, most preferred 5 to 45 ppm. Other anionic stabilizers may be a very strong acid including without limitation perchloric acid, hydrochloric acid, hydrobromic acid, toluenesulfonic acid, fluorosulfonic acid, phosphoric acid, ortho, meta, or para-phosphoric acid, trichloroacetic acid, and sulfuric acid.

In embodiments of the present invention, the preferred free radical stabilizer is butylated hydroxyl anisole (BHA). Other free radical stabilizers include without limitation, hydroquinone; catechol; hydroquinone monomethyl ether and hindered phenols such as butylated hydroxyanisol; 4-ethoxyphenol; butylated hydroxytoluene (BHT, 2,6-di-tert-butyl butylphenol), 4-methoxyphenol (MP); 3-methoxyphenol; 2-tert-butyl-4-methoxyphenol; 2,2-methylene-bis-(4-methyl-6-tert-butylphenol). The free radical stabilizer is preferably employed in an amount of from about 200 to about 15000 ppm, more preferably from about 1000 to about 10000 ppm, and even more preferably from about 2000 to about 8000 ppm.

In embodiments, the adhesive compositions may optionally include at least one plasticizing agent that imparts flexibility to the polymer formed from the monomer. The plasticizing agent is one which preferably does not contain any moisture and should not adversely affect the stability of the compositions. Suitable plasticizers include, but are not limited to, tributyl citrate (TBC), acetyl tributyl citrate (ATBC), dimethyl sebacate, triethyl phosphate, tri(2-ethyl-hexyl) phosphate, tri(p-cresyl) phosphate, diisodecyl adipate (DIDA), glyceryl triacetate, glyceryl tributyrate, dioctyl adipate (DICA), isopropyl myrisate, butyl state, lauric acid, trioctyl trimellitate, dioctyl glutarate and mixtures thereof. Tributyl citrate, diisodecyl adipate and acetyl tributyl citrate are preferred plasticizers. The amount of plasticizer, when present can be up to thirty percent (30%) of the total weight of the adhesive composition. The amount of plasticizer to be used can be determined by one of ordinary skill in the art using known techniques without undue experimentation.

A polymerization accelerator may also be included in the final adhesive composition. Suitable polymerization accelerators are calixarenes and oxacalixarenes, silacrowns, crownethers, cyclodextrin and its derivatives, polyethers, aliphatic alcohol, various aliphatic carboxylic acid esters, benzoyl peroxide, amine compounds such as triethyl amine, diethyl amine, butyl amine, isopropyl amine, tributyl amine, N,N-dimethyl aniline, N,N-diethyl aniline, N,N-dimethyl-p-toluidine, N,N-dimethyl-m-toluidine, N,N-dimethyl-o-toluidine, dimethyl benzyl amine, pyridine, picoline, vinyl pyridine, ethanolamine, propanolamine and ethylene diamine, quaternary ammonium salts such as alkyl ammonium salts, amide-bonded ammonium salts, ester-bonded ammonium salts such as alkylammonium salts, amide-bonded ammonium salts, ester-bonded ammonium salts, salts and alkylimidazolinium salts, cyclosulfur compounds and derivatives, and polyalkylene oxides and derivatives.

Suitable crown ethers include, but are not limited to, 15-crown-5,18-crown-6, dibenzo-18-crown-6, tribenzo-18-crown-6, dicyclohexyl-18-crown-6, benzo-15-crown 5, dibenzo-24-crown-8, dibenzo-30-crown-10, asym-dibenzo-22-crown-6, dimethylsila-11 crown-4, dimethylsila-14-crown-5, dimethylsila-17-crown-6, dibenzo-14-crown-4, dicyclohexyl 24-crown-8, asym-dibenzo-22-crown-6, cyclohexyl-12-crown-4, 1,2-decalyl-15-crown-5, 1,2 naphtho-15-crown-5,3,4,5-naphthyl-16-crown-5, 1,2-methyl-benzo-18-crown-6, 1,2-methylbenzo-5,6-methylbenzo-18-crown-6, 1,2-t-butyl-18-crown-6, 1,2-vinyl benzo-15-crown-5, 1,2-vinylbenzo-18-crown-6, 1,24-butyl-cyclohexyl-18-crown-6, and 1,2-benzo-1,4-benzo-5 oxygen-20-crown-7. The preferred crown ether is 18-crown-6.

The adhesive compositions of the present invention may also include thickening agents. Suitable thickening agents include polycyanoacrylate, partial polymer of cyanoacrylate, polycaprolactone, copolymers of alkylacrylate and vinyl acetate, polyalkyl methacrylates, polyalkyl acrylates, lactic-glycolic acid copolymers, lactic acid-caprolactone copolymers, polyorthoesters, copolymers of alkyl methacrylates and butadiene, polyoxalates, and triblock copolymers of polyoxypropylene flanked by two hydrophilic chains of polyoxyethylene. The preferred thickening agent can be a partial polymer of cyanoacrylate as disclosed in U.S. patent application Ser. No. 12/214,791. Preferred thickening agents can also be triblock copolymers of polyoxyalkylene as disclosed in U.S. patent application Ser. No. 12/214,794. Preferably the thickening agent is miscible in cyanoacrylate monomer compositions at room temperature.

The compositions of this invention may further contain colorants such as dyes, pigments, and pigment dyes. Suitable dyes include derivatives of anthracene and other complex structures. These dyes include without limitation, 1-hydroxy-444 methylphenylamino]-9,10 anthracenedione (D&C violet No. 2); 9-(o-carboxyphenyl)-6-hydroxy-2,4,5,7-tetraiodo-3H-xanthen-3-one-, disodium salt, monohydrate (FD&C Red No. 3); disodium salt of 6-hydroxy-5-[(4-sulfophenyl)axo]-2-naphthalene-sulfonic acid (FD&C Yellow No. 6); 2(1,3-dihydro-3-oxo-5-sulfo-2H-indole-2-ylidine)-2,3-dihydro-3-oxo-1H-ind-ole-5 sulfonic acid disodium salt (FD&C Blue No. 2); and 1,4-bis(4-methylanilino)anthracene-9,10-dione (D&C Green No. 6).

The method of the present invention comprises subjecting the cyanoacrylate adhesive composition to at least one filtration step (thus, at least one filter) under an inert and moisture-free atmosphere such as, for example, medical grade nitrogen. This step functions to reduce the bioburden of the cyanoacrylate adhesive composition prior to gamma sterilization according to the present invention. The at least one filter preferably has a pore size of from about 1 to about 200 micrometers, more preferably from about 1 to about 100 micrometers, and even more preferably from about 2 to about 50 micrometers. The second and additional filters preferably have a pore size of from about 0.01 to about 10 micrometers, more preferably from about 0.05 to about 10 micrometers, and even more preferably from about 0.05 to about 2 micrometers. Medical grade nitrogen, for example, has a purity of at least 99%, preferably 99.5% and more preferably 99.8%.

The cyanoacrylate compositions used in the methods of this invention are prepared by conventional techniques of mixing the appropriate components until homogenous.

The specific viscosity of these compositions depends, in part, on the intended application of the composition. For example, relatively low viscosities are often preferred where application is to be made to a large surface area (e.g., abdominal surfaces). This preference results from the fact that those forms are less viscous and, accordingly, will permit more facile large surface area application of a thin film. Contrarily, where application is to be made to a specific position on the skin (e.g., elbow surfaces, knee surfaces and the like), higher viscosity compositions, including those containing thixotropic materials, are preferred to prevent "running" of the compositions to unintended locations.

Accordingly, these compositions have a viscosity of from about 2 to about 50,000 centipoise at 20° C. Preferably the less viscous compositions have a viscosity of from about 2 to about 1,500 centipoise at 20° C. More preferably, the cyanoacrylate ester employed in these compositions is almost entirely in monomeric form and the composition has a viscosity of from about 2 to about 100 centipoise at 20° C.

The method of the present invention comprises the step of adding the cyanoacrylate adhesive composition from (a) to individual packaging elements. A suitable individual packaging element containing the cyanoacrylate to be sterilized by gamma irradiation is preferably one of multi-layer construction of different materials such as those described in, for example, U.S. patent application Publication No. 2005/0147582, the entirety of which is incorporated herein by reference. The container or package may be of any shape enabling delivery of the cyanoacrylate for its intended use. For example, the container may be shaped as pouches, bottles, applicators, vials, syringes, ampoules and the like. However, whatever its construction or shape, it is important that the inner most layer in contact with the cyanoacrylate is composed of a nitrile polymer. The multi-layer construction of the container may be any combination of any material suitable for storage and delivery of a liquid adhesive composition. By way of example, suitable materials include polymers, copolymers, thermoplastic polymers, plastics, nitrile polymers and copolymers, and metal, preferably foil.

Suitable thermoplastic polymers include the polyolefins, which include but are not limited to polyethylene (PE), and polypropylene (PP), and polyesters, such as, polyethylene terephthalate (PET). Any class of polyethylenes are suitable, including high density polyethylene (HDPE), high density cross-linked polyethylene (HDXLPE), cross-linked polyethylene (XLPE), medium density polyethylene (MDPE), linear low density polyethylene (LLDPE), low density polyethylene (LDPE), and very low density polyethylene (VLDPE), high molecular weight polyethylene (HMWPE), ultra low molecular weight polyethylene (ULMWPE) and ultra high molecular weight polyethylene (UHMWPE). Representative densities of certain polyethylenes are as follows: LDPE-0.910-0.925 g/cm$^3$; MDPE-0.926-0.940 g/cm$^3$; HDPE-0.941-0.965 g/cm$^3$. Other densities can be determined by the ordinary artisan by referencing ASTM D 1248 (1989).

Preferred are homopolymers of polyethylene although suitable copolymers of vinyl acetate or acrylates may be used. Suitable polypropylenes are typically homopolymers, although random copolymer (PPCO) and block copolymers with other thermoplastic monomers may be used. Any commercially available packaging or film PET is suitable, including polyethylene terephthalate G copolymer (PETG) and oriented PET. Other suitable polymers include polycarbonate (PC), polyallomer (PA), polymethylpentene (PMP or TPX) polyketone (PK), polystyrene (PS), polyvinylchloride (PVC), naphthalate, polybutylene terephthalate, thermoplastic elastomer (TPE), mixtures thereof, and the like.

Suitable nitrile polymers and copolymers include nitrile polymers produced by polymerizing a major proportion of a monounsaturated nitrile and a minor proportion of another monovinyl monomer or indene copolymerizable, nitrile polymers produced by polymerizing a major portion of a monounsaturated nitrile and a minor portion of another monovinyl monomer or indene copolymerizable therewith in the presence of a diene rubber, polyacrylates, polymethacrylate, polyalkyl methacrylates, polyethers, polysiloxanes, polysulfones, polyphenylene sulfide, polyether ether ketones, thermoplastic polyimides, polybenzimidazoles, polyquinoxalones, polyoxazolines, styrene-acrylonitrile copolymer and acrylonitrile-butadiene-styrene copolymer, vinyl acetate containing polymers, maleic anhydride containing polymers, butadiene and/or isoprene based elastomers, acrylonitrile, and methacrylonitrile. Preferred are nitrite copolymers including preferably a copolymer of acrylonitrile and methyl acrylate, which is a product commercially available from BP America, BP Chemicals, Barex® Resin Division, Lima, Ohio, U.S.A. and is sold by the brand name "Barex®". Barex® resins are generally produced by the copolymerization of acrylonitrile and methyl acrylate in a 75:25 ratio onto a nitrile rubber backbone, which is used to provide impact strength. The refractive index of the nitrile rubber is matched to the polymer matrix in order to maintain transparency. The ISO abbreviation for Barex® resins is A/MA/B; its three main components being acrylonitrile, methyl acrylate, and butadiene.

The container may be constructed such that the layers of materials may be any number of layers in any order, however it is important that the inner layer in contact with the liquid adhesive is a nitrile polymer or acrylonitrile copolymer.

In a preferred embodiment, the container comprises two parts, namely a top section and a bottom section, each comprising two or more layers, preferably two or three layers. The top section or front cover is one comprising three layers wherein the inner layer comprises a nitrile polymer, the middle layer comprises polypropylene and the outer layer comprises polyethylene or alternatively, the front cover may comprise an inner layer of nitrile polymer and an outer layer of polypropylene. The bottom section or backing foil preferably also is one comprising three layers, preferably an inner layer of nitrile polymer, a middle layer of foil and an outer layer of polyethylene terephthalate. Alternatively, the bottom section is one comprising an inner layer of nitrile polymer and an outer layer of aluminum foil.

The container size may vary depending on the volume of liquid it contains. The amount of liquid can vary depending on the end use or particular application, including from 0.1 mL to 10 mL. Preferably the container is constructed as an applicator for applying medical adhesive to living tissue and has a reservoir area for housing the liquid adhesive and an applicator surface through which the liquid is dispensed, such as a sponge material, which may also vary in size depending on the particular use or application for the adhesive. Preferably about sixty (60) to eighty (80) percent of the applicator's volume is filled with the liquid adhesive. The different layers of material may suitably have a thickness of from about 5 to about 1000 micrometers.

In preferred embodiments of the present invention, the bioburden of the package or container of the cyanoacrylate adhesive composition is further reduced by sterilization by exposure to ethylene oxide (ETO) gas prior to Gamma sterilization. Before injecting ETO to the chamber, the container with cyanoacrylate adhesive are preferably preconditioned with a humidity ranging from about 30% to about 80%, preferably from about 40% to about 80%, and more preferably from about 40% to about 70%. The duration of the exposure of the container including cyanoacrylate adhesives to ETO gas is preferably from about 40 minutes to about 600 minutes, more preferably from about 60 minutes to about 500 minutes, and even more preferably from about 70 minutes to about 400 minutes. Any ETO residue can be removed by, for example, aeration using a nitrogen wash for at least 3 times, and more preferably at least 5 times.

The method of the present invention also comprises the step of packaging the individual packaging elements (containing the cyanoacrylate adhesive composition) into at least one outer package having a density. Cyanoacrylate adhesive compositions in a suitable container such as, for example, an applicator with an overpack can be sterilized by low dosage of Gamma irradiation in different configurations. Such container preferably contains adhesive compositions in an amount of, for example, from about 0.1 mL to about 10 mL, preferably from about 0.1 mL to about 5 mL, and more preferably from about 0.2 mL to about 5 mL. For example, cyanoacrylate-based compositions in a preferred container can be put into a unit box first and then stored in a second outer box for Gamma sterilization at different dosages. The unit box can include from about 2 to about 30 suitable containers with cyanoacrylate-based compositions, preferably from about 4 to about 25 suitable containers, and more preferably from about 5 to about 20 suitable containers. The outer box can include from about 3 to about 50 unit boxes, preferably from about 5 to about 40 unit boxes, and more preferably from about 5 to about 30 unit boxes. Preferably, the total density of the individual packaging elements and the at least one outer package can range from about 0.05 to about 0.6 g/cm$^3$, preferably from about 0.05 to 0.5 g/cm$^3$, and more preferably from about 0.05 to 0.40 g/cm$^3$.

In another embodiment, cyanoacrylate-based adhesive compositions can be gamma-sterilized at the low doses described herein in a box containing a large amount of suitable containers. The box can include from about 200 to about 4,000 suitable containers comprising cyanoacrylate adhesive compositions, preferably from about 300 to about 3,000 suitable containers, and more preferably from about 400 to 2,500 suitable containers. The density of the box containing a large amount of suitable container (including the density of the individual containers) can range from about 0.04 to about 0.4 g/cm$^3$, preferably from about 0.05 to about 0.4 g/cm$^3$, and more preferably from about 0.05 to about 0.3 g/cm$^3$. A number of boxes including a large amount as described above of suitable containers with adhesive compositions can be placed in a carrier that is exposed to Gamma irradiation at low doses according to the present invention. For example, one carrier can hold from about 10 to about 50 boxes, preferably from about 10 to about 40 boxes, and more preferably from about 12 to about 40 boxes. This way, cyanoacrylate adhesive compositions can be sterilized on a large production scale, which makes the sterilization process quick and efficient with a shorter turn-around time compared to other irradiation sterilization techniques such as E-beam sterilization.

The method of the present invention also includes the step of sterilizing the cyanoacrylate adhesive composition and the individual packaging elements by exposing the individual packaging elements to gamma radiation at a dose of from about 5 to about 20 kGy, wherein the total density of the individual packaging elements and the at least one outer package is from about 0.05 to about 0.6 gm/cm$^3$. Standard Cobalt Co-60 may be used as the gamma ray source in sterilizing the compositions and packages of the present invention. The dose of gamma irradiation desirably ranges from about 5 to about 20 kGy, preferably in the range of about 5 to about 18 kGy, and more preferably in the range of about 5 to about 15 kGy. In other embodiments of the present invention, the dose of gamma radiation is in the range of from about 5 to about 10 kGy. In other embodiments of the present invention, the dose of gamma radiation is in the range of from about 10 to about 15 kGy. In still other embodiment, the dose of gamma irradiation can be as low as 5 kGy and still sufficiently sterilize the adhesive compositions which are prepared and packaged as disclosed herein.

As disclosed herein, gamma sterilization of cyanoacrylate-based compositions results in almost no change in the viscosity of the composition, indicating that no or very little premature polymerization of cyanoacrylates occurs upon low dose gamma sterilization in the instant invention, making them particularly suitable for medical applications. The viscosity of cyanoacrylate compositions was measured by a Brookfield DV-II+ viscometer, before and after gamma sterilization with various low doses, and the results are summarized in Table 1. The results show only slight decreases or increases in viscosity, within the measurement error of the viscometer, of the inventive cyanoacrylate compositions gamma sterilized in the invention package or container. Viscosity is expressed in centipoise (cps).

As shown in Table 1 above, the integrity of the adhesive composition is maintained upon gamma sterilization, as confirmed by no or negligible change in viscosity after gamma irradiation. This is in contrast to the prior art U.S. Pat. No. 5,530,037 to McDonnell et al. which reports a 400% or more increase in viscosity resulting from gamma sterilization at the minimum dose of 25 kGy. The compositions and package of the present invention minimize the variation in viscosity of cyanoacrylate adhesive brought about by gamma sterilization.

The package and its contents should be sterile, meaning that the composition is free from viable microorganisms. In preferred embodiments of the present invention, the composition is sterilized to provide a Sterility Assurance Level (SAL) of at least $10^{-3}$, which means that the probability of a single unit being non-sterile after sterilization is 1 in 1000. In embodiments, the Sterility Assurance Level may be at least $10^{-4}$, or may be at least $10^{-5}$, or preferably, the sterility assurance level should be at least $10^{-6}$.

The sterility of the above cyanoacrylate compositions treated by lower doses of gamma irradiation set forth above, was analyzed by Bacteriostasis and Fungistasis tests, whereby the sterilized compositions were challenged with microorganisms such as *Bacillus subtilis, Candida albicans*, and *Aspergillus niger* in different mediums. No growth of the microorganisms was observed in either Soybean-Casein Digest Medium (SCDM) or Fluid Thioglycollate Medium (FTM), as shown in Table 2. This indicates the sterility of the cyanoacrylate adhesive compositions sterilized by low dose gamma irradiation.

TABLE 2

Sterility results of different samples sterilized by Gamma irradiation at various dosages

| Lot number of SURGISEAL | Dose range (kGy) | Sterility result | |
|---|---|---|---|
| | | Number of Growth in FTM | Number of Growth in SCDM |
| 1a | 15.4-16.4 | 0 | 0 |
| 1a | 16.6-18.0 | 0 | 0 |
| 1a | 18.7-19.9 | 0 | 0 |
| 1d | 16.6-18.0 | 0 | 0 |

TABLE 1

Viscosity of cyanoacrylate adhesive compositions before and after low dose gamma irradiation sterilization.

| Sample | Dosage range (kGy) | Before Gamma irradiation | | | | After Gamma irradiation | | | |
|---|---|---|---|---|---|---|---|---|---|
| | | 1 | 2 | 3 | average | 1 | 2 | 3 | average |
| 1a | 18.7-19.9 | 9.81 | 9.81 | 7.97 | 9.20 | 9.19 | 7.36 | 9.19 | 8.58 |
| 1a | 15.4-16.4 | 9.81 | 9.81 | 7.97 | 9.20 | 7.97 | 7.36 | 9.19 | 8.17 |
| 1b | 11.7-13.0 | 7.36 | 7.97 | 7.97 | 7.77 | 6.13 | 7.36 | 5.52 | 6.34 |
| 1b | 5.0-5.6 | 7.36 | 7.97 | 7.97 | 7.77 | 7.97 | 7.36 | 7.36 | 7.56 |
| 1c | 11.7-13.0 | 7.36 | 7.97 | 6.13 | 7.15 | 6.74 | 6.13 | 6.13 | 6.33 |
| 1c | 5.0-5.6 | 7.36 | 7.97 | 6.13 | 7.15 | 6.13 | 6.74 | 7.97 | 6.95 |
| 1d | 11.7-13.0 | 6.74 | 7.36 | 6.74 | 6.95 | 7.36 | 8.58 | 6.74 | 7.56 |
| 1d | 5.0-5.6 | 6.74 | 7.36 | 6.74 | 6.95 | 6.74 | 7.36 | 7.97 | 7.36 |
| 1e | 11.82-13.45 | 5.52 | 6.74 | 6.74 | 6.33 | 6.74 | 6.13 | 5.52 | 6.13 |
| 1f | 11.82-13.45 | 6.13 | 5.52 | 6.13 | 5.93 | 5.52 | 6.13 | 6.13 | 5.93 |
| 1g | 11.82-13.45 | 6.13 | 6.74 | 5.52 | 6.13 | 6.13 | 5.52 | 5.52 | 5.72 |
| 1e | 12.4-14.6 | 6.13 | 5.52 | 5.52 | 5.72 | 6.13 | 5.52 | 6.13 | 5.93 |
| 1f | 12.4-14.6 | 5.52 | 5.52 | 6.13 | 5.72 | 6.74 | 6.74 | 6.13 | 6.54 |
| 1g | 12.4-14.6 | 6.74 | 6.13 | 6.13 | 6.33 | 5.52 | 6.13 | 6.74 | 6.13 |

TABLE 2-continued

Sterility results of different samples sterilized by Gamma irradiation at various dosages

| Lot number of SURGISEAL | Dose range (kGy) | Sterility result Number of Growth in FTM | Number of Growth in SCDM |
|---|---|---|---|
| 1e | 11.82-13.45 | 0 | 0 |
| 1f | 11.82-13.45 | 0 | 0 |
| 1g | 11.82-13.45 | 0 | 0 |
| 1e | 12.4-14.6 | 0 | 0 |
| 1f | 12.4-14.6 | 0 | 0 |
| 1g | 12.4-14.6 | 0 | 0 |
| 1h | 5.0-5.6 | 0 | 0 |
| 1h | 11.7-13.0 | 0 | 0 |

Besides being stable and sterile, the adhesives or microbial sealants used in medical applications should have a shelf-life of at least one year and, preferably, two years. According to embodiments of the present invention, the cyanoacrylate adhesive compositions after gamma sterilization provide a suitable shelf life for use in the medical field. The shelf life stability of inventive sterilized cyanoacrylate adhesive compositions was evaluated by an accelerated aging study, performed in an oven at 80° C. for a period of 13 days. Based on ASTM F1980 13 days accelerated aging at 80° C. is equal to 2 years of shelf life, and 1 day of accelerated aging at 80° C. is equal to 56 days. Samples from Table 1 were gamma irradiated at various dosage ranges. Viscosity measurements are reported as average viscosity after gamma irradiation at different intervals of the accelerated aging at 80° C. The results are summarized in Table 3 below.

TABLE 3

The viscosity of cyanoacrylate adhesive compositions sterilized by gamma irradiation at different dose ranges, at different intervals of the accelerated aging at 80° C.

| Sample | Dosage range (kGy) | Average viscosity (cps) at different intervals of the accelerated aging at 80° C. | | |
|---|---|---|---|---|
| | | Day 0 | Day 6 | Day 13 |
| 1a | 5.0-5.6 | 7.4 | N/A | 10.6 |
| 1b | 5.0-5.6 | 7.6 | 7.8 | 16.1 |
| 1c | 5.0-5.6 | 6.9 | N/A | 14.3 |
| 1a | 11.7-13.0 | 7.2 | N/A | 27.4 |
| 1e | 11.82-13.45 | 6.1 | 8.8 | 14.7 |
| 1f | 11.82-13.45 | 5.9 | 7.2 | 18.4 |
| 1e | 12.4-14.6 | 5.9 | 7.4 (Day 8) | 14.9 |
| 1f | 12.4-14.6 | 6.5 | 8.8 (Day 8) | 15.1 |
| 1f | 15.9-17.4 | 9.0 | 9.4 | 27.8 |
| 1e | 16.0-16.7 | 5.9 | 11.2 (Day 7) | 21.3 |
| 1a | 18.7-19.9 | 9.20 | 15.5 | 57.8 |

As shown in Table 3, the viscosity of the cyanoacrylate adhesive compositions after gamma sterilization at different dosage levels increased as the accelerated aging proceeded, however the viscosity levels remained within values which did not affect the performance of the compositions as adhesives. Specifically, the increase in viscosity at the end of the accelerated aging period did not affect the set time performance of the adhesive compositions or the ability to dispense the compositions from their applicators. This data indicates that the cyanoacrylate adhesive compositions of the present invention, treated by low dose gamma irradiation, provide a shelf life of at least two (2) years, making them useful as medical devices.

All irradiation treatments in the following examples were carried out in conventional manner at ambient temperature.

The viscosity of the cyanoacrylate compositions was measured by a Brookfield DV-II+ viscometer. About 0.5 ml of a cyanoacrylate composition was put into the cup and the cup was brought into position and slowly secured with the retaining arm. The motor was turned on after the sample was equilibrated in the cup. The viscosity of the compositions was measured in triplicate. The spindle and cup were cleaned with acetone after each measurement.

The methods of this invention are useful in providing sterilized cyanoacrylate compositions which can then be used for topical application to mammalian skin with reduced risk of introducing microbes onto the skin and, accordingly, reduced risk of infection. This is particularly important where topical application is onto skin areas which are already broken (e.g., small topical skin wounds or closing the surgical incision site) or which will become broken (e.g., application to form a surgical incise drape which will then be broken by the incision initiating the surgery).

The following examples are provided for the purpose of further illustrating the present invention but are by no means intended to limit the same.

EXAMPLES

Example 1

The setting time of the inventive adhesives was measured using an in vitro pig skin test. A 4×4 inch section of pig skin was prepared by wiping the surface of the skin with sterile gauze saturated with isopropanol to remove all oily substances. The surface was then wiped with sterile gauze to remove the isopropanol. An applicator containing cyanoacrylate was opened and adhesive was permitted to saturate the applicator sponge for about 10 seconds prior to application. A thin film was applied to the pig skin after which elapsed time was recorded by a stop watch. Set time was then recorded by stopping the clock when the film was dry as determined at the point where no liquid transfer occurred when the film was touched with a gloved finger. The adhesive composition (Composition 1, the inventive 2-octyl cyanoacrylate including a trace amount of crown ether polymerization initiator) was packaged in the inventive applicators and sterilized by gamma irradiation at doses of 15.4-16.4 kGy and 18.7-19.9 kGy, respectively. Table 4 shows the set time of packaged Composition 1 after gamma sterilization at two different dose ranges. The result indicates that gamma sterilization caused little or no change in the set time of the cyanoacrylate adhesive composition.

TABLE 4

Set time measurement of composition 1 in the preferred package after Gamma sterilization at 15.4-16.4 and 18.7-19.9 kGy, respectively.

| Treatment | Set Time (Second) | | | |
|---|---|---|---|---|
| | Test 1 | Test 2 | Test 3 | Average |
| Before sterilization | 17 | 18 | 20 | 18.3 |
| Gamma sterilization 15.4-16.4 kGy | 17 | 19 | 17 | 17.7 |
| Gamma sterilization 18.7-19.9 kGy | 17 | 19 | 20 | 18.7 |

Example 2

2-octyl cyanoacrylate monomer was treated with polyvinylpyrrolidone, stabilized with free radical and anionic polymerization inhibitors, and mixed with 7.8 ppm of the colorant and a trace amount of polymerization accelerator. In a polyethylene bottle, 121.8 g of this 2-octyl cyanoacrylate composition was mixed with 12.2 mg of DC violet #2 dye at room temperature for three (3) hours. The cyanoacrylate composition was injected into an applicator of the invention having an inner layer of acrylonitrile copolymer and was sealed with an Adhesive Tech™ glue gun. Applicators containing the cyanoacrylate were then exposed to gamma irradiation. The viscosity of the cyanoacrylate composition after gamma sterilization at doses of 5.0-5.6 kGy or 11.7-13.0 kGy was measured to be 8.17 cps and 6.95 cps, respectively, as compared to an initial viscosity prior to sterilization of 6.53 cps.

Example 3

In a polyethylene bottle, 124.3 g 2-octyl cyanoacrylate composition, treated as in example 2, was mixed with 6.2 mg of DC Green #6 at room temperature for 3 hours. The cyanoacrylate composition was injected into the inventive applicator with acrylonitrile copolymer as the inner layer, and was sealed with Adhesive Tech™ glue gun. Applicators containing the cyanoacrylate composition were then exposed to gamma irradiation. The viscosity of this cyanoacrylate composition after gamma sterilization at doses of 5.0-5.6 kGy or 11.7-13.0 kGy was 6.74 cps and 6.33 cps, respectively, compared to 6.32 cps before gamma sterilization.

Example 4

2-octyl cyanoacrylate monomer was treated with polyvinylpyrrolidone and stabilized with free radical and anionic polymerization inhibitors, to which 7.8 ppm of DC violet #2 was added. 844.6 g of such 2-octyl cyanoacrylate composition was mixed with a trace amount of 18-crown-6 polymerization accelerator in a high density polyethylene bottle at room temperature for 3 hours. The bulk cyanoacrylate composition was then packaged in the inventive package or applicator and placed into a secondary plastic bubble package. Applicators containing the cyanoacrylate composition were then exposed to gamma irradiation. The viscosity of the cyanoacrylate composition after gamma sterilization at doses of 5.0-5.6 or 11.713.0 kGy was 7.56 and 6.34 cps, respectively, compared to 7.77 cps before gamma sterilization.

Example 5

In a polyethylene bottle, 126.4 g 2-octyl cyanoacrylate composition, treated as in example 2, was mixed with 5.1 mg of DC Violet #2 at room temperature for 3 hours. The cyanoacrylate composition was injected into the inventive applicator with acrylonitrile copolymer as the inner layer, and was sealed with an Adhesive Tech™ glue gun. The applicator containing the cyanoacrylate composition was then exposed to gamma irradiation. The viscosity of this cyanoacrylate composition after gamma sterilization at doses of 5.0-5.6 kGy and 11.7-13.0 kGy was 7.15 cps and 6.54 cps, respectively, compared to 6.53 cps before gamma sterilization.

Example 6

In a polyethylene bottle, 119.6 g 2-octyl cyanoacrylate composition, treated as in example 2, was mixed with 3.6 mg of DC Green #6 at room temperature for 3 hours. The cyanoacrylate composition was injected into the inventive applicator with acrylonitrile copolymer as the inner layer, which was sealed with an Adhesive Tech™ glue gun. Applicators containing the cyanoacrylate composition were then exposed to gamma irradiation. The viscosity of the cyanoacrylate composition after gamma sterilization at doses of 5.0-5.6 kGy or 11.7-13.0 kGy was 6.74 cps and 6.95 cps, respectively, compared to 6.44 cps before gamma sterilization.

Example 7

2-octyl cyanoacrylate monomer was treated with polyvinylpyrrolidone and re-stabilized with free radical and anionic polymerization inhibitors, to which 7.8 ppm of DC violet #2 was added. 81 lb of such 2-octyl cyanoacrylate composition was mixed with a trace amount of 18-crown-6 polymerization accelerator in a stainless steel container equipped with the mechanical agitator at room temperature. The bulk cyanoacrylate composition was packaged in an inventive primary applicator and placed into a secondary package as described above. Applicators containing the cyanoacrylate composition were then exposed to gamma irradiation. The viscosity of the cyanoacrylate composition after gamma sterilization at doses of 15.4-16.4 kGy or 18.7-19.9 kGy was 8.17 cps and 8.58 cps, respectively, compared to 9.20 cps before gamma sterilization.

Example 8

The sterility of the cyanoacrylate compositions sterilized by gamma irradiation at 5.0-5.6 kGy, 11.7-13.0 kGy, 15.4-16.4 kGy, and 18.7-19.9 kGy, respectively, was evaluated by the USP bacteriostasis and fungistasis testing using the direct transfer method. Test samples were immersed into 500 mL of Soybean Casein Digest Medium (SCDM) or Fluid Thioglycollate Medium (FTM). The test microorganism, such as *Bacillus subtilis*, *Candida albican*, or *Aspergillus niger*, was inoculated into each of the test sample containers and into a positive control container of the same medium at less than 100 colony forming units. All preparations were performed in an aseptic manner within a filtered clean bench. In order to obtain a quantitative measure of each microorganism, a duplicate plate count was performed. After inoculation, the test sample and positive control container were incubated in SCDM at 20-25° C. and in FTM at 30-35° C. for 14 days. Inoculated containers were observed periodically throughout the incubation period. Growth of the challenging microorganism was used to indicate the sterility. No growth in both SCDM and FTM indicated that the test adhesive composition was sterile.

Example 9

2-octyl cyanoacrylate monomer was treated with polyvinylpyrrolidone, stabilized with free radical and anionic polymerization inhibitors, and mixed with DC Violet #2 as the colorant. 45.8 lb of such 2-octyl cyanoacrylate composition was mixed with a trace amount of the polymerization accelerator in a stainless steel container equipped with the mechanical agitator at room temperature to prepare adhesive sample 1e. The bulk cyanoacrylate composition was packaged in a primary applicator and placed into a secondary package as described above. Applicators containing the cyanoacrylate composition were then exposed to gamma irradiation. The viscosity of the cyanoacrylate composition after gamma sterilization at dose range of 11.82-13.45 kGy was 6.13 cps, compared to 6.33 cps before gamma sterilization.

Example 10

2-octyl cyanoacrylate monomer was treated with polyvinylpyrrolidone, stabilized with free radical and anionic polymerization inhibitors, and mixed with DC Violet #2 as the colorant. 19.36 lb of such 2-octyl cyanoacrylate composition was mixed with a trace amount of the polymerization accelerator in a stainless steel container equipped with the mechanical agitator at room temperature to prepare adhesive sample 1f. The bulk cyanoacrylate composition was packaged in an inventive primary applicator and placed into a secondary package as described above. Applicators containing the cyanoacrylate composition were then exposed to gamma irradiation. The viscosity of the cyanoacrylate composition after gamma sterilization at dose range of 12.4-14.6 kGy was 6.54 cps, compared to 5.72 cps before gamma sterilization.

While the present invention has been described with an emphasis upon preferred embodiments, it will be obvious to those of ordinary skill in the art that variations in the preferred cyanoacrylate compositions and methods may be used and that it is intended that the invention may be practiced otherwise than as specifically described herein. Accordingly, the present invention includes all modifications encompassed within the spirit and scope of the invention as defined by the claims that follow.

We claim:

1. A method for sterilizing a cyanoacrylate monomer adhesive composition, comprising adding a filtered cyanoacrylate monomer adhesive composition comprising monomeric 2-octyl cyanoacrylate, about 2 to about 50 ppm of sulfur dioxide, about 200 to about 15,000 ppm of butylated hydroxyl anisole and, optionally, 18-crown-6 crown ether to individual packaging elements, each individual packaging element comprising multiple layers, wherein the inner-most layer comprises a copolymer of acrylonitrile and methyl acrylate in a ratio of acrylonitrile to methyl acrylate of 75:25; packaging the individual packaging elements into a container, thereby forming a package; and irradiating the package with gamma radiation at a dose of from about 5 to about 10 k Gy, thereby sterilizing the package, wherein the-cyanoacrylate monomer adhesive contained within the container does not cure upon gamma irradiation and for at least two years of shelf storage thereafter.

2. The method of claim 1, wherein the cyanoacrylate monomer adhesive composition is filtered through a first filter having a pore size of from about 1 to about 200 µm.

3. The method of claim 1, wherein the density of the individual packaging elements and the container is from about 0.05 to about 0.5 gm/cm$^3$.

4. The method of claim 3, wherein the density of the individual packaging elements and the container is from about 0.05 to about 0.40 gm/cm$^3$.

5. The method of claim 1, wherein the dose of gamma radiation is about 5 k Gy.

6. The method of claim 1, wherein the cyanoacrylate monomer adhesive composition is filtered through a first filter and then through a second filter having a pore size of from about 0.01 to about 10 µm while under an inert and moisture-free atmosphere.

7. The method of claim 1, wherein the cyanoacrylate monomer adhesive composition comprises 18-crown-6 crown ether.

8. The method of claim 1, wherein the cyanoacrylate monomer adhesive composition comprises 5 to 45 ppm of sulfur dioxide and 2000 to 8000 ppm of butylated hydroxyl anisole.

9. A method for sterilizing a cyanoacrylate monomer composition, comprising adding a filtered cyanoacrylate monomer composition comprising monomeric n-butyl cyanoacrylate, monomeric 2-octyl cyanoacrylate, or a mixture of monomeric n-butyl cyanoacrylate and monomeric 2-octyl cyanoacrylate, from about 5 ppm to about 50 ppm of sulfur dioxide, from about 1000 to about 15,000 ppm of butylated hydroxyl anisole and, optionally, 18-crown-6 crown ether to a package comprising multiple layers, wherein the inner-most layer comprises a copolymer of acrylonitrile and methyl acrylate in a ratio of acrylonitrile to methyl acrylate of 75:25; and
    irradiating said package containing said cyanoacrylate monomer composition with gamma radiation at a dose of from about 5 to about 10 kGy, wherein the cyanoacrylate monomer adhesive contained within the package does not cure upon gamma irradiation and for at least two years of shelf storage thereafter.

10. The method of claim 9, wherein the cyanoacrylate monomer composition is filtered through a first filter having a pore size of from about 1 to about 200 µm.

11. The method of claim 9, wherein the density of the package is from about 0.05 to about 0.5 gm/cm$^3$.

12. The method of claim 11, wherein the density of the package is from about 0.0.05 to about 0.40 gm/cm$^3$.

13. The method of claim 9, wherein the dose of gamma radiation is about 5 k Gy.

14. The method of claim 9, wherein the cyanoacrylate monomer adhesive composition is filtered through a first filter and then through a second filter having a pore size of from about 0.01 to about 10 µm while under an inert and moisture-free atmosphere.

15. The method of claim 9, wherein the cyanoacrylate monomer composition comprises a crown ether.

16. The method of claim 9, wherein the cyanoacrylate monomer composition comprises 5 to 45 ppm of sulfur dioxide and 2000 to 8000 ppm of butylated hydroxyl anisole.

17. The method of claim 16, wherein the composition comprises monomeric n-butyl cyanoacrylate.

* * * * *